United States Patent
Anderson

(10) Patent No.: US 12,127,940 B2
(45) Date of Patent: Oct. 29, 2024

(54) PREDISPOSED ANNULUS PATCH FOR VALVE REPAIR IMPLANT

(71) Applicant: Boston Scientific Scimed, Inc., Maple Grove, MN (US)

(72) Inventor: James M. Anderson, Corcoran, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 285 days.

(21) Appl. No.: 17/474,675

(22) Filed: Sep. 14, 2021

(65) Prior Publication Data

US 2022/0079759 A1 Mar. 17, 2022

Related U.S. Application Data

(60) Provisional application No. 63/079,597, filed on Sep. 17, 2020.

(51) Int. Cl.
*A61F 2/24* (2006.01)

(52) U.S. Cl.
CPC .................................. *A61F 2/2445* (2013.01)

(58) Field of Classification Search
CPC ........ A61F 2/24; A61F 2/2409; A61F 2/2445; A61F 2/243; A61F 2230/0091; A61F 2220/0016; A61F 2/2442; A61F 2250/0006; A61F 2/2412; A61F 2/2427; A61F 2/2457
See application file for complete search history.

(56) References Cited

U.S. PATENT DOCUMENTS

| | | | |
|---|---|---|---|
| 9,180,005 B1 * | 11/2015 | Lashinski | A61F 2/2442 |
| 9,848,983 B2 | 12/2017 | Lashinski et al. | |
| 10,172,708 B2 | 1/2019 | Anderson | |
| 10,543,088 B2 * | 1/2020 | Lashinski | A61F 2/2466 |
| 10,543,090 B2 * | 1/2020 | Griswold | A61B 17/0469 |
| 10,849,755 B2 * | 12/2020 | Lashinski | A61F 2/2466 |
| 11,191,656 B2 * | 12/2021 | Sirhan | A61F 2/90 |
| 11,642,221 B2 * | 5/2023 | Doran | A61F 2/2445 |
| | | | 623/2.36 |
| 11,723,770 B2 * | 8/2023 | Inouye | A61F 2/2466 |
| | | | 623/2.36 |

(Continued)

FOREIGN PATENT DOCUMENTS

WO 2021026184 A1 2/2021

*Primary Examiner* — Seema Mathew
(74) *Attorney, Agent, or Firm* — Seager, Tufte & Wickhem, LLP

(57) ABSTRACT

A patch for interposing between an implantable device and a treatment site, such as to inhibit migration (e.g., lateral shifting) of the implantable device with respect to the treatment site without interfering with contact of the implantable device with the treatment site, and/or to reduce (and preferably inhibit or prevent) damage to tissue at the treatment site and/or movement of the anchor element (used to anchor the implantable device) with respect to the treatment site. The patch may extend continuously around the perimeter of the device, or discontinuously as more than one patch. The patch may be delivered on the implantable device to the treatment site, or separately delivered and deployed before the implantable device is delivered and deployed, the implantable device being implanted over the patch and the treatment site.

20 Claims, 10 Drawing Sheets

(56) References Cited

U.S. PATENT DOCUMENTS

| | | | |
|---|---|---|---|
| 2008/0077235 A1* | 3/2008 | Kirson | A61F 2/2418 623/2.11 |
| 2008/0125861 A1* | 5/2008 | Webler | A61B 17/064 623/2.36 |
| 2011/0060407 A1* | 3/2011 | Ketai | A61B 17/0644 623/2.37 |
| 2012/0022644 A1* | 1/2012 | Reich | A61F 2/2466 623/2.37 |
| 2014/0222136 A1* | 8/2014 | Geist | A61F 2/2412 623/2.37 |
| 2016/0235526 A1* | 8/2016 | Lashinski | A61F 2/2409 |
| 2017/0135816 A1* | 5/2017 | Lashinski | A61F 2/2466 |
| 2018/0228610 A1* | 8/2018 | Lashinski | A61F 2/2466 |
| 2018/0263777 A1* | 9/2018 | Gross | A61F 2/2445 |
| 2019/0029827 A1* | 1/2019 | Bar | A61F 2/24 |
| 2020/0289265 A1* | 9/2020 | Gifford, III | A61F 2/2448 |
| 2021/0220136 A1* | 7/2021 | Krumpelmann | A61B 17/0401 |
| 2021/0228349 A1* | 7/2021 | Vidlund | A61F 2/2457 |
| 2022/0079759 A1* | 3/2022 | Anderson | A61F 2/2445 |
| 2022/0079761 A1* | 3/2022 | Pearson | A61F 2/2463 |
| 2022/0079762 A1* | 3/2022 | Serina | A61F 2/2445 |
| 2023/0121200 A1* | 4/2023 | Inouye | A61F 2/2445 623/2.11 |
| 2024/0156598 A1* | 5/2024 | Oliver | A61B 5/02158 |

\* cited by examiner

PREDISPOSED ANNULUS PATCH FOR VALVE REPAIR IMPLANT

PRIORITY

The present application is a non-provisional of, and claims the benefit of priority under 35 U.S.C. § 119 to, U.S. Provisional Application Ser. No. 63/079,597, filed Sep. 17, 2020, the disclosure of which is hereby incorporated herein by reference in its entirety for all purposes.

FIELD

The present disclosure relates generally to the field of implantable medical devices. In particular, the present disclosure relates to medical devices, systems, and methods for annuloplasty and other cardiac treatment techniques.

BACKGROUND

Mitral insufficiency (MI) (also referred to as mitral regurgitation or mitral incompetence) is a form of heart disease where the mitral annulus dilates excessively and the valve leaflets no longer effectively close, or coapt, during systolic contraction. Regurgitation of blood occurs during ventricular contraction and cardiac output may decrease as a result. Surgical and endoluminal annuloplasty techniques have been introduced that aim to restore a mitral valve to its native or an improved configuration, for example by implanting an annuloplasty ring or other implantable device around the valve annulus.

Devices and systems and methods which may reinforce or strengthen the positioning or connection of an implantable device in an implant site, and/or reduce migration (shifting or loosening) of the implantable device with respect to the treatment site, and/or reduce potential tissue damage at the treatment site (such as when the implantable device is cinched to modify the valve annulus configuration, or later after the procedure has been completed) are desirable.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary.

In accordance with various principles of the present disclosure, a heart valve implant device is described, the device including a frame having a proximal end and a distal end and configured to be implanted in a valve annulus surrounding a heart valve with the distal end secured to the valve annulus, and a patch carried by the distal end of the frame to be positioned between the frame and the valve annulus when the frame is secured to the valve annulus.

In some embodiments, the frame includes a plurality of distal apices formed at the distal end thereof, with the frame secured to the valve annulus along the distal apices, and the patch positioned along at least one of the distal apices to be positioned between the at least one of the distal apices and the valve annulus when the frame is secured to the valve annulus.

In some embodiments, the patch includes one or more patches discontinuously extending about a perimeter of the frame. Additionally or alternatively, the frame further includes a plurality of anchors, each anchor positioned at a distal apex of the frame, and at least one of the patches is carried by an anchor at a distal apex of the frame.

In some embodiments, the patch extends substantially continuously about a perimeter of the frame.

In some embodiments, the frame is configured to move between a collapsed delivery configuration and an expanded configuration and positions therebetween to modify the shape of a valve annulus to which the frame is secured.

In some embodiments, the patch is configured to collapse and fold with the frame when the frame is in a collapsed delivery configuration.

In some embodiments, the patch extends substantially continuously about a perimeter of the frame.

In some embodiments, the frame includes a plurality of struts joined along proximal apices at the proximal end of the frame and distal apices along the distal end of the frame, and the frame further includes a plurality of anchors, each anchor positioned at a distal apex of the frame, and at least one of the anchors carries the patch. In some embodiments, the patch includes one or more patches discontinuously extending about a perimeter of the frame, at least one of the patches being carried by an anchor.

In accordance with various principles of the present disclosure, a system for implanting an implantable device at a treatment site within a body is described, the system including an implantable device, a patch positionable between the implantable device and the treatment site, and a deployment device configured to secure the implantable device over the patch and to the treatment site.

In some embodiments, the patch is carried by the implantable device, and the deployment device is also a delivery device configured to deliver the implantable device and the patch to the treatment site.

In some embodiments, the system further includes a delivery device configured to deliver the patch to the treatment site, where the deployment device is also a delivery device configured to deliver the implantable device to the treatment site, to deploy the implantable device over the patch, and to implant the implantable device into the treatment site.

In some embodiments, the patch is configured to extend around a perimeter of the treatment site. In some embodiments, the patch is a substantially continuous ring configured to extend continuously around the perimeter of the treatment site. In other embodiments, the patch is configured to extend discontinuously around the perimeter of the treatment site.

In some embodiments, the implantable device is an annuloplasty device configured to move between a collapsed delivery configuration and an expanded configuration and positions therebetween to modify the shape of a valve annulus.

In accordance with another aspect, the present subject matter is directed to an annuloplasty method including deploying an annulus patch around a valve annulus, deploying a heart valve implant device over the annulus patch, and implanting the heart valve implant device into the valve annulus with the annulus patch positioned between the valve annulus and portions of heart valve implant device engaging the valve annulus via the annulus patch. In some embodiments, the method further includes delivering the annulus patch with the heart valve implant device to the valve annulus. In some embodiments, the method further includes delivering and deploying the annulus patch before delivering and deploying the heart valve implant device These and other features and advantages of the present disclosure, will be readily apparent from the following detailed description, the scope of the claimed invention being set out in the appended claims. While the following disclosure is presented in terms of aspects or embodiments, it should be appreciated that individual aspects can be claimed separately or in combination with aspects and features of that embodiment or any other embodiment.

BRIEF DESCRIPTION OF THE DRAWINGS

Non-limiting embodiments of the present disclosure are described by way of example with reference to the accompanying drawings, which are schematic and not intended to be drawn to scale. The accompanying drawings are provided for purposes of illustration only, and the dimensions, positions, order, and relative sizes reflected in the figures in the drawings may vary. For example, devices may be enlarged so that detail is discernable, but is intended to be scaled down in relation to, e.g., fit within a working channel of a delivery catheter or endoscope. In the figures, identical or nearly identical or equivalent elements are typically represented by the same reference characters, and similar elements are typically designated with similar reference numbers differing in increments of 100, with redundant description omitted. For purposes of clarity and simplicity, not every element is labeled in every figure, nor is every element of each embodiment shown where illustration is not necessary to allow those of ordinary skill in the art to understand the disclosure.

The detailed description will be better understood in conjunction with the accompanying drawings, wherein like reference characters represent like elements, as follows.

DETAILED DESCRIPTION

Figure 1:
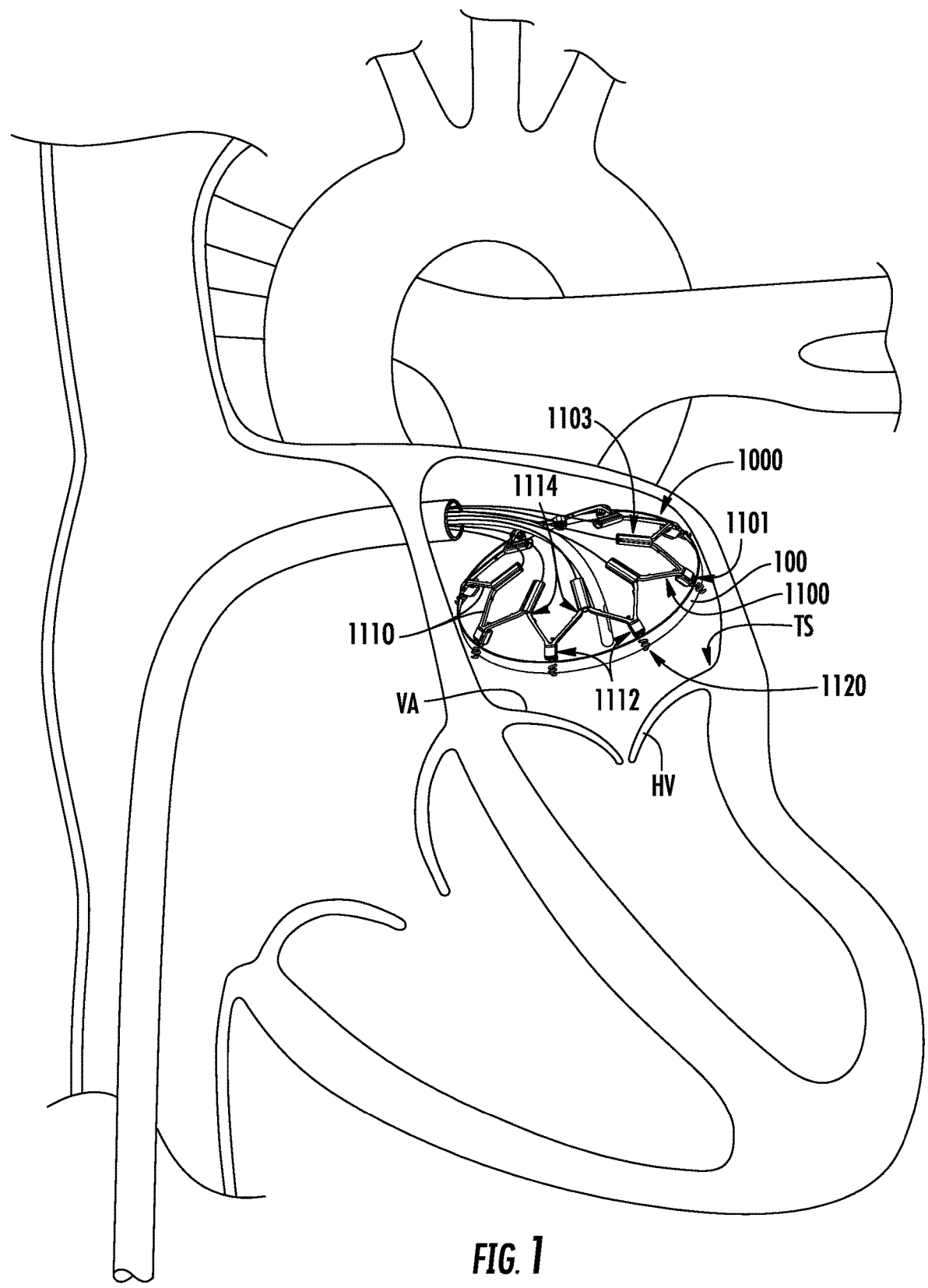
FIG. 1 is a schematic view of a human heart with an example of a heart valve implant device shown being implanted at the mitral valve annulus with an annulus patch formed in accordance with various aspects of the present disclosure.

The following detailed description should be read with reference to the drawings, which depict illustrative embodiments. It is to be understood that the disclosure is not limited to the particular embodiments described, as such may vary. All apparatuses and systems and methods discussed herein are examples of apparatuses and/or systems and/or methods implemented in accordance with one or more principles of this disclosure. Each example of an embodiment is provided by way of explanation and is not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure. In fact, it will be apparent to those skilled in the art that various modifications and variations can be made in the present disclosure without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the appended claims and their equivalents.

It will be appreciated that the present disclosure is set forth in various levels of detail in this application. In certain instances, details that are not necessary for one of ordinary skill in the art to understand the disclosure, or that render other details difficult to perceive may have been omitted. The terminology used herein is for the purpose of describing particular embodiments only, and is not intended to be limiting beyond the scope of the appended claims. Unless defined otherwise, technical terms used herein are to be understood as commonly understood by one of ordinary skill in the art to which the disclosure belongs. All of the devices and/or methods disclosed and claimed herein can be made and executed without undue experimentation in light of the present disclosure.

As used herein, "proximal" refers to the direction or location closest to the user (medical professional or clinician or technician or operator or physician, etc., such terms being used interchangeably without intent to limit or otherwise), etc., such as when using a device (e.g., introducing the device into a patient, or during implantation, positioning, or delivery), and "distal" refers to the direction or location furthest from the user, such as when using the device (e.g., introducing the device into a patient, or during implantation, positioning, or delivery). "Longitudinal" means extending along the longer or larger dimension of an element. "Central" means at least generally bisecting a center point, and a "central axis" means, with respect to an opening, a line that at least generally bisects a center point of the opening, extending longitudinally along the length of the opening when the opening comprises, for example, a tubular element, a strut, a channel, or a bore.

In accordance with various aspect of the present disclosure, a valve annulus patch is provided in conjunction with an implantable device, such as a heart valve implant device which may be used to treat (e.g., repair) a heart valve, such as by an annuloplasty procedure. It will be appreciated that embodiments described herein with reference to the drawings are with reference to a heart valve implant device, though principles of the present disclosure may be applied to other types or forms of implantable devices. The patch may be deployed in accordance with various aspects of the present disclosure to prevent migration (e.g., shifting) of the implantable device (such as resulting from migration or tear out of the anchor) and/or tearing of (or other damage to) the annulus tissue (e.g., caused by movement of a heart valve implant device, which may cause abrasion or other damage to the valve annulus tissue) and/or anchor migration (e.g., backout or other movement of the anchor element used to anchor a heart valve implant device with respect to the valve annulus, which may allow loosening of the heart valve implant device relative to the valve annulus and/or migration of the heart valve implant device). The patch may not only protect against tissue tearing (such as during or after implant of the device to the treatment site TS), but may also promote tissue growth which may expedite natural tissue securement of the implantable device at the treatment site TS.

The patch may be in the form of a film, such as a biologically acceptable film, such as a polymeric film. For instance, biocompatible, biostable materials such as urethanes or polyurethanes or polymers may be used, such as with elongations of approximately 100-600%. In some embodiments, the patches may be in the form of membranes with a thickness of at least about of 10 μm and at most about 1 mm (including increments of 0.1 μm therebetween). In some embodiments, the patch is configured with features to facilitate mechanical coupling to the tissue, such as micro-hooks (e.g., metal, polymer, ceramic rigid features that hook, pinch or mechanically grip tissue) or a mesh (e.g., PET mesh) configuration allowing (or promoting) tissue growth therein. For instance, electrospun polymer fibers, woven or braided mesh, and/or fibers ranging in thickness from at least approximately 10 um to at most approximately 250 um (including increments of 0.1 μm therebetween) may be used. The fibers may allow stretching or bias in a selected axis to allow or limit the amount of stretching or compliance, i.e., radial expansion limited, or lateral expansion/limitations. In some embodiments, some fibers of the patch may be substantially rigid, such as ceramic or polycarbonate. In some embodiments, the patch is configured to provide instant adhesion to the treatment site (e.g., for acute therapy) and/or to promote tissue ingrowth (e.g., for chronic support). In some embodiments the annulus patch is elastic or semi-elastic, such as with an elongation of approximately 100-600%, and may impart a degree of contracting force to the treatment site, such as to contribute to valve annulus reduction in an annuloplasty or valve repair procedure.

In some embodiments, the patch extends around the entire perimeter of the valve annulus and/or around the entire perimeter of the heart valve implant device, and may be in the form of a substantially continuous ring (which may be noncircular such as following the general outer contour of a heart valve). In some embodiments, the patch may be deployed at selected locations about the valve annulus and/or heart valve implant device, such as at points of contact therebetween and/or points at which the heart valve implant device is implanted or anchored into the treatment site. Preferably, the dimensions of the patch are selected for the patch to extend beyond the contact area of the implantable device with the treatment site. For instance, the width of patch to be placed on a valve annulus (in a direction extending from the valve to the outside perimeter of the valve annulus) may be greater than the width of the heart valve implant device to form a suitable barrier and/or to provide suitable protection and/or reinforcement and/or anti-migration features, etc. If anchor elements are provided to anchor the heart valve implant device to the valve annulus, the annulus patch may have narrower portions along regions between the anchor element if such regions are not engaged or do not otherwise interact with the heart valve implant device. Embodiments in which the patch does not extend around the perimeter of the heart valve implant device (e.g., is not a continuous ring), and is provided at one or more anchor elements, then the patch may be shaped and/or sized and/or configured to be larger than the surface area of the anchor element contacting the treatment site.

A patch formed in accordance with principles of the present disclosure may be delivered with the heart valve implant device, such as carried by the heart valve implant device, to the heart valve to be treated. For instance, the patch may be carried by the heart valve implant device. Alternatively, the patch may be delivered before delivery of the heart valve implant device. The patch may be implanted before the heart valve implant device is delivered, or implanted at the same time the heart valve implant device is implanted. In some embodiments, tissue ingrowth is permitted. In some embodiments, it may be desirable to pre-dilatate the annulus with a balloon, or to pre-implant the patch. For instance, patch implantation may be performed with various current valvuloplasty procedures in which the valve or annulus may be remodeled and diseased valves/annulus may be torn and/or calcified disease cracked open to allow proper fitting of valve prosthesis.

The patch may interact with the implantable device such as to reduce movement of a portion of the implantable device relative to the patch. For instance, the patch may be coupled to the implantable device such as with an adhesive (e.g., with light adhesive tackiness) and/or quick tear-away sutures and/or micro-suction cups and/or similar mechanisms known or heretofore known to those of ordinary skill in the art for coupling/retaining implantable elements together. Alternatively or additionally, the patch may be structured and/or configured to reinforce annulus tissue. In some embodiments, the patch may be adhered to the annulus, such as with the use of adhesives and/or micro-hooks and/or micro-barbs and/or fish scales and/or suction cups and/or thrombogenic material and/or materials promoting tissue growth or ingrowth. In some embodiments, the patch may be formed to induce tissue ingrowth so that the patch does not move relative to the annulus tissue.

Various embodiments of a heart valve annulus patch, such as for use with a heart valve implant device, will now be described with reference to examples illustrated in the accompanying drawings. Reference in this specification to "one embodiment," "an embodiment," "some embodiments", "other embodiments", etc. indicates that one or more particular features, structures, and/or characteristics in accordance with principles of the present disclosure may be included in connection with the embodiment. However, such references do not necessarily mean that all embodiments include the particular features, structures, and/or characteristics, or that an embodiment includes all features, structures, and/or characteristics. Some embodiments may include one or more such features, structures, and/or characteristics, in various combinations thereof. Moreover, references to "one embodiment," "an embodiment," "some embodiments", "other embodiments", etc. in various places in the specification are not necessarily all referring to the same embodiment, nor are separate or alternative embodiments necessarily mutually exclusive of other embodiments. When particular features, structures, and/or characteristics are described in connection with one embodiment, it should be understood that such features, structures, and/or characteristics may also be used in connection with other embodiments whether or not explicitly described, unless clearly stated to the contrary. It should further be understood that such features, structures, and/or characteristics may be used or present singly or in various combinations with one another to create alternative embodiments which are considered part of the present disclosure, as it would be too cumbersome to describe all of the numerous possible combinations and subcombinations of features, structures, and/or characteristics. Moreover, various features, structures, and/or characteristics are described which may be exhibited by some embodiments and not by others. Similarly, various features, structures, and/or characteristics or requirements are described which may be features, structures, and/or characteristics or requirements for some embodiments but may not be features, structures, and/or characteristics or requirements for other embodiments. Therefore, the present invention is not limited to only the embodiments specifically described herein.

Turning now to the drawings, it will be appreciated that in the following description, elements or components similar among the various illustrated embodiments are generally designated with the same reference numbers increased by 100 and redundant description is omitted. Common features are identified by common reference elements and, for the sake of brevity, the descriptions of the common features are generally not repeated. For purposes of clarity, not all components having the same reference number are numbered.

Figure 2:
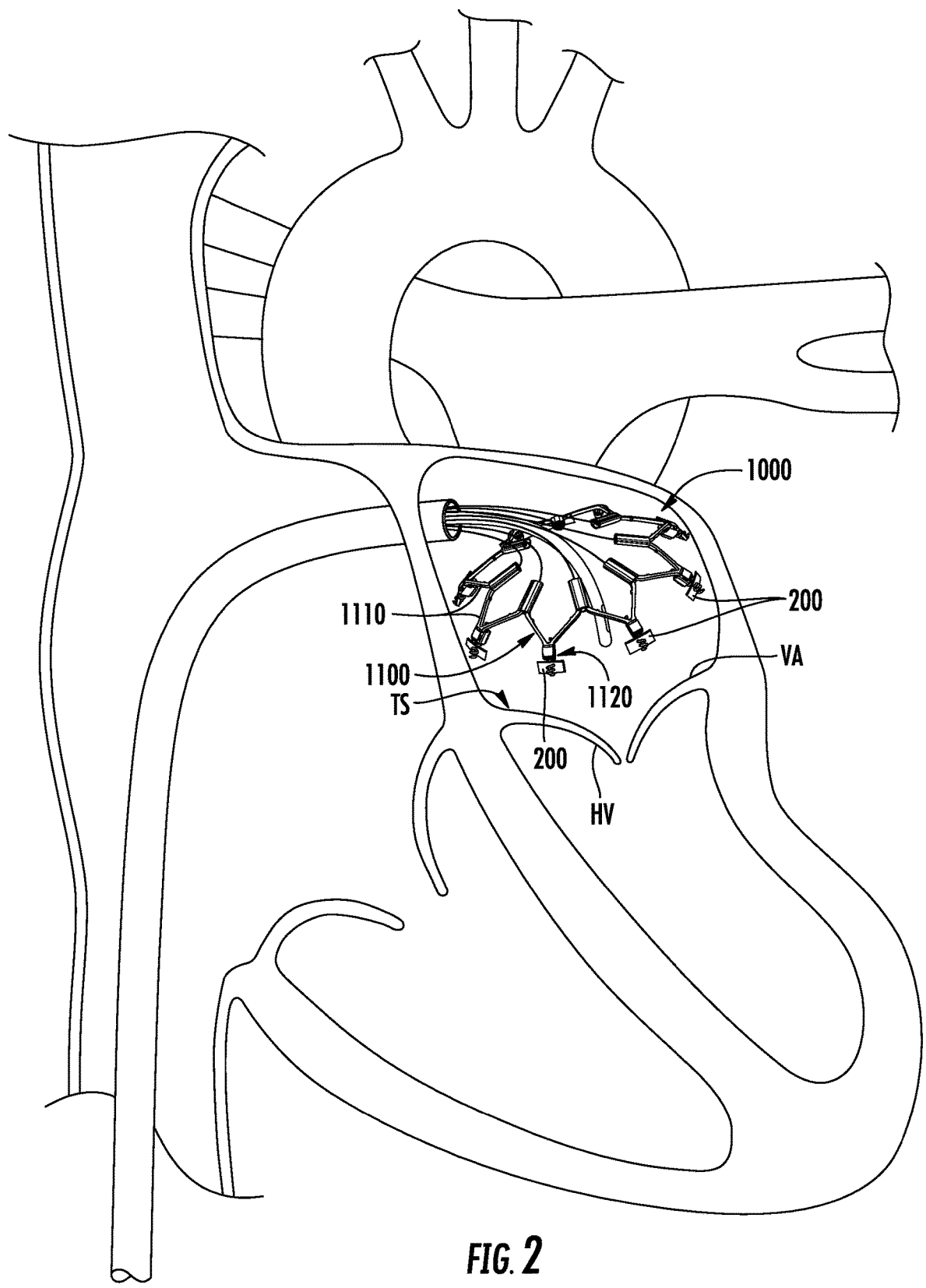
FIG. 2 is a schematic view of a human heart with an example of a heart valve implant device shown being implanted at the mitral valve annulus with another annulus patch formed in accordance with various aspects of the present disclosure.

Examples of an annulus patch 100, 200 formed in accordance with principles of the present disclosure and associated with an example of a heart valve implant device 1000 are illustrated in FIG. 1 and FIG. 2 implanted in a valve annulus VA around a heart valve HV. In accordance with various principles of the present disclosure, the annulus patches 100, 200, or at least portions thereof, are positioned between the heart valve implant device 1000 and the valve annulus VA in which the heart valve implant device 1000 is implanted. The annulus patch 100, 200 may provide generalized protection to the valve annulus tissue and/or provide a barrier between the heart valve implant device 1000 (such as to protect the valve annulus VA from any potential abrasions or undue pressure from the heart valve implant device 1000) and/or reinforce the valve annulus tissue (such as from tears or to reinforce against movement of the heart valve implant device 1000 or portions thereof, such as anchor elements thereof, relative to the valve annulus tissue).

As may be appreciated, the annulus patch 100, 200 may have a varying extent around the perimeter of the heart valve implant device 1000. For instance, the annulus patch 100 illustrated in FIG. 1 extends around the entire heart valve implant device 100, whereas the annulus patch 200 illustrated in FIG. 2 extends discontinuously around the perimeter. More particularly, the annulus patch 100 illustrated in FIG. 1 may be in the form of a substantially continuous ring, such as following the shape or contour of (e.g., the shape of the perimeter of) the treatment site TS, whereas the annulus patch 200 illustrated in FIG. 2 may have one or more separate patches or segments spaced apart from one another around the treatment site TS. In accordance with various principles of the present disclosure, in the embodiment of FIG. 2, at least one of the separate patches or segments of the annulus patch 200 is provided between the valve annulus VA and a portion of the heart valve implant device 1000 engaging the valve annulus VA (e.g., via the annulus patch 200).

Figure 4:
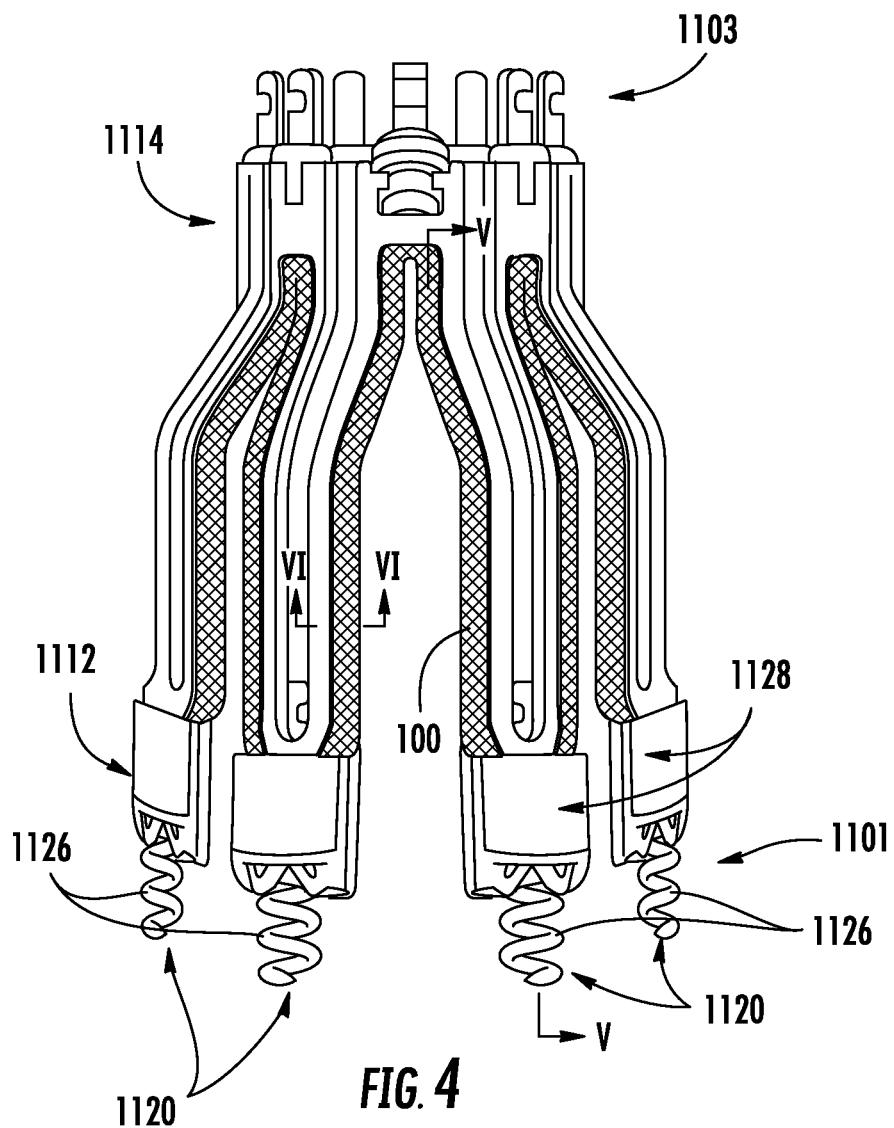
FIG. 4 is a perspective view of an example of a heart valve implant device in a closed configuration for delivery and carrying an annulus patch in accordance with various aspects of the present disclosure.

In the illustrated embodiments, the heart valve implant device 1000 is an implant device for annuloplasty, such as for custom modifying or reshaping of a heart valve (e.g., the mitral valve, as illustrated, or the tricuspid valve), capable of moving between a compressed or retracted or collapsed delivery configuration (as illustrated in FIG. 4, configured to fit within a delivery device navigated through tortuous and/or narrow passages in the body, such as the vascular system) and an expanded configuration (as illustrated in FIGS. 1 and 2). The heart valve implant device 1000 is capable of moving between (in either direction) the collapsed and expanded configurations and positions therebetween to modify the shape of the valve annulus VA at which it is implanted/to which it is secured.

Figure 3:
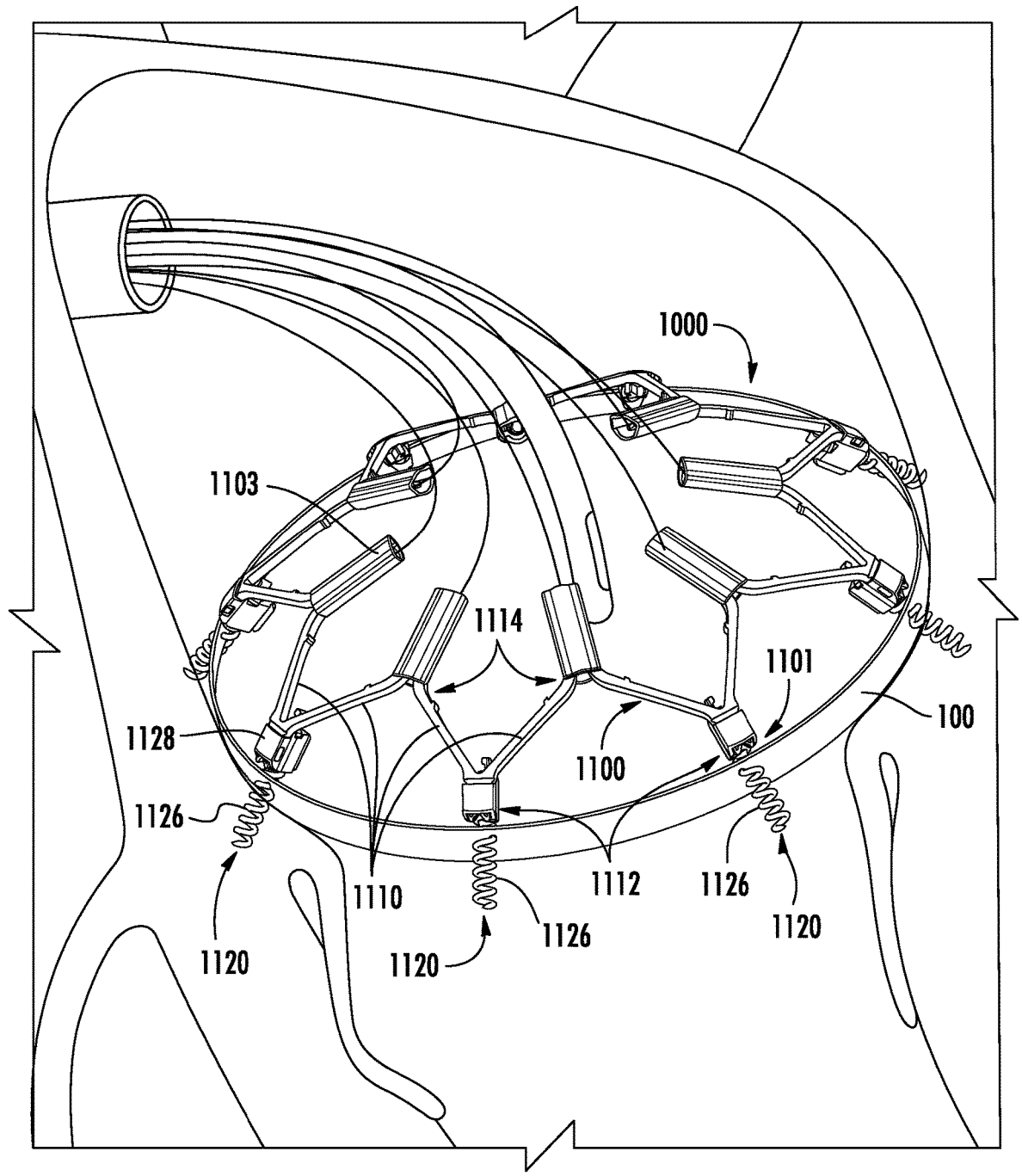
FIG. 3 is a perspective view of an example of a heart valve implant device with an embodiment of an annulus patch as in FIG. 1, shown in a delivered configuration.

Features of an example of an implantable device 1000 may be better appreciated with reference to FIG. 3, showing an embodiment of an annulus patch 100 on an example of a heart valve implant device 1000 in a delivered configuration. The heart valve implant device 1000 includes a frame member 1100 that may be disposed about a heart valve or other cardiac feature. The frame member 1100 may be generally symmetrical with respect to the central frame axis FA although it need not be symmetrical. The frame member 1100 may form a generally tubular shape, where herein "tubular" includes circular as well as other rounded or otherwise closed shapes. The frame member 1100 may be configured to change shape, size, and/or configuration. For example, the frame member 1100 may assume various shapes, sizes, configurations etc. during different phases of deployment such as during pre-delivery, delivery, tissue engagement, anchoring, and adjustment (e.g., cinching).

The frame member 1100 may be formed from one or more struts 1110 that may form all or part of the frame member 1100. The struts 1110 may include elongated structural members formed of a metal alloy, a shape memory material, such as an alloy of nickel titanium or other metals, metal alloys, plastics, polymers, composites, other suitable materials, or combinations thereof. In one embodiment, the struts 1110 may be formed from the same, monolithic piece of material (e.g., tube stock). Thus, reference to struts 1110 may refer to different portions of the same, extensive component. Alternatively, reference to struts 1110 may refer to components that are formed separately and attached together (optionally permanently, such as by welding or other methods). In some embodiments, the struts 1110 may be separate components that are detachably coupled to form distal apices 1112 and proximal apices 1114. Alternatively, if formed from a monolithic piece of material, the material may be cut or otherwise formed to define distal apices 1112 and proximal apices 1114. The frame member 1100 may be considered to be substantially tubular, and configured to change shape, size, dimensions, and/or configuration. For example, the frame member 1100 may assume various shapes, sizes, dimensions, configurations, etc. during different phases of deployment such as during pre-delivery, delivery, tissue engagement, anchoring, and adjustment (e.g., cinching). It will be appreciated that alternate configurations of the frame member 1100, such as depending on the manner and orientation in which the implantable device 1000 is delivered, are within the scope and spirit of the present disclosure.

As illustrated in FIG. 3, a plurality of anchors 1120 are carried at a distal end 1101 of the frame member 1100, such as along the distal apices 1112 of the frame member 1100. In the illustrated embodiments, the distal end 1101 of the frame member 1100 is the end closer to the treatment site TS (e.g., valve annulus VA), such as to be engaged directly or indirectly (e.g., with an annulus patch as disclosed herein between the distal end 1101 of the frame member 1100 and the treatment site TS), and the proximal end 1103 of the frame member 1100 is the end furthest from the valve annulus VA (e.g., directed proximally toward, and optionally engaged with, a delivery/deployment system used to deliver and/or deploy the frame member 1100). Generally, each anchor 1120 is associated with a different distal apex 1112. The anchors 1120 (e.g., such as upon rotation of the anchors 1120) are distally advanced with respect to the frame member 1100 into the valve annulus VA to implant or to adjust the position of the frame member 1100, and withdrawn to remove or to adjust the position of the frame member 1100. In some embodiments the anchors 1120 may translate through an anchor housing 1128 coupled to the frame member 1100. The anchor shaft 1126 (such as in the form of a helical shaft) may be coupled to and extend through a portion of an associated distal apex 1112, with or without an associated anchor housing 1128. In view of the above, and with reference to FIGS. 1 and 2, an annulus patch 100, 200 formed in accordance with principles of the present disclosure preferably is positioned between the valve annulus VA and a distal apex 1112 of the frame member 1100 from which an anchor 1120 extends to anchor the frame member 1100 to the valve annulus VA.

As further illustrated FIG. 3, a plurality of collars or cinch collars or sliders or nuts 1130 (such terms being used interchangeably herein without intent to limit, reference being made generally to collars for the sake of convenience) are carried at a proximal end 1103 of the frame member 1100, such as along the proximal apices 1114 of the frame member 1100. Generally, each collar 1130 is associated with a different proximal apex 1114. One or more of the collars 1130 may be advanced along the struts 1110, distally or proximally with respect to the apex over which the collar 1130 is positioned, to adjust the relative positions of the struts 1110 joined at such apex. Such adjustment results in adjustment of at least one of the size, shape, configuration, dimension, etc. of the frame member 1100 (e.g., retraction/compression or expansion of the frame upon bringing adjacent struts 1110 closer or further apart, respectively) to affect at least one of the size, shape, configuration, dimension, etc. of the valve annulus VA (such as to restore or correct the shape of a valve annulus VA for proper functioning or competency thereof).

Various additional features of an implantable device as illustrated in FIG. 3, as well as related delivery systems and methods of use, and mechanisms for positioning anchors for annular reconstruction, may be appreciated with reference to the following patents and patent applications, each of which is incorporated herein by reference in its entirety for all purposes: U.S. Patent Application Publication No. 2010/0249920, published Sep. 30, 2010, titled "DEVICE FOR TRANSLUMENAL RESHAPING OF A MITRAL VALVE ANNULUS"; U.S. Pat. No. 9,180,005, issued Nov. 10, 2015, titled "ADJUSTABLE ENDOLUMINAL MITRAL VALVE RING"; U.S. Pat. No. 9,192,471, issued Nov. 24, 2015, titled "DEVICE FOR TRANSLUMENAL RESHAPING OF A MITRAL VALVE ANNULUS"; U.S. Pat. No. 9,610,156, issued Apr. 4, 2017, titled "MITRAL VALVE INVERSION PROSTHESES"; U.S. Pat. No. 9,795,480, issued Oct. 24, 2017, titled "RECONFIGURING TISSUE FEATURES OF A HEART ANNULUS"; U.S. Pat. No. 9,848,983, issued Dec. 26, 2017, titled "VALVE REPLACEMENT USING ROTATIONAL ANCHORS"; U.S. Pat. No. 10,321,999, issued Jun. 18, 2019 titled "SYSTEMS AND METHODS FOR RESHAPING A HEART VALVE"; U.S. Pat. No. 10,335,275, issued Jul. 2, 2019, titled "METHODS FOR DELIVERY OF HEART VALVE DEVICES USING INTRAVASCULAR ULTRASOUND IMAGING"; U.S. Pat. No. 10,548,731, issued Feb. 4, 2020, titled "IMPLANTABLE DEVICE AND DELIVERY SYSTEM FOR RESHAPING A HEART VALVE ANNULUS"; and/or U.S. Pat. No. 10,555,813, issued Feb. 11, 2020, titled "IMPLANTABLE DEVICE AND DELIVERY SYSTEM FOR RESHAPING A HEART VALVE ANNULUS".

A heart valve implant device 1000, such as (but not limited to) with a frame member 1100 illustrated in FIG. 3, is generally delivered to the treatment site TS in a compressed or retracted delivery configuration as illustrated in FIG. 4. The delivery system may include a delivery sheath or catheter 1200 (such terms being used interchangeably herein without intent to limit) which may be navigated through a tortuous pathway (e.g., through vasculature of the leg, neck, or arm) through the patient to the treatment site TS (e.g., a heart valve, such as the mitral valve). A guidewire 1210 may extend from a distal end 1201 of the delivery catheter 1200 and may be used to navigate the distal end 1201 of the delivery catheter 1200 to the treatment site TS to deploy the heart valve implant device 1000. In some embodiments, an intravascular cardiac echography (ICE) catheter 1300 (e.g., extending through the delivery catheter 1200 and the heart valve implant device 1000) may be used to monitor placement of the heart valve implant device 1000 during deployment and implantation. An example of a steerable delivery device and system with various positioning and imaging capabilities is described in U.S. Pat. No. 10,335,275, titled "METHODS FOR DEPLOYMENT OF HEART VALVE DEVICES USING INTRAVASCULAR ULTRASOUND IMAGING", and issued on Jul. 2, 2019, which patent is incorporated herein by reference in its entirety for all purposes. The heart valve implant device 1000 is generally carried in a compressed configuration within the delivery catheter 1200 and is released from the distal end 1201 of the delivery catheter 1200, for example by expelling the heart valve implant device 1000 from the delivery catheter 1200 or withdrawing the delivery catheter 1200 to expose the heart valve implant device 1000. The heart valve implant device 1000 may then be positioned at a treatment site TS, such as a location proximate to, surrounding, or partially surrounding a valve annulus VA, and manipulated into the desired configuration for implantation into and modification of (e.g., repair of) the valve annulus VA.

Figure 5:
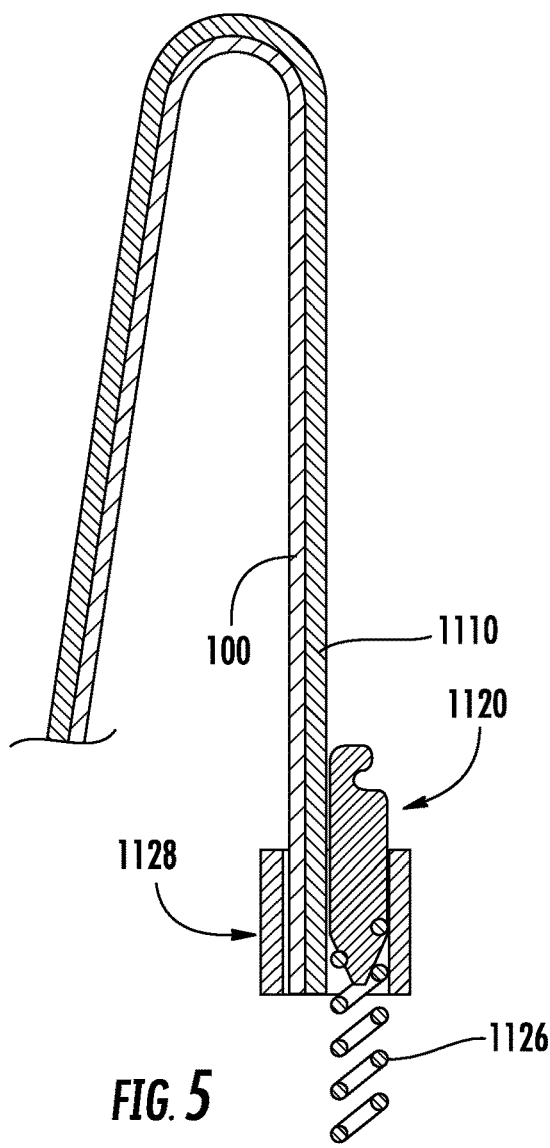
FIG. 5 is a cross-sectional view along line V-V in FIG. 4 of a portion of a strut of a heart valve implant with an annulus patch formed in accordance with various principles of the present disclosure provided thereon.
Figure 6:
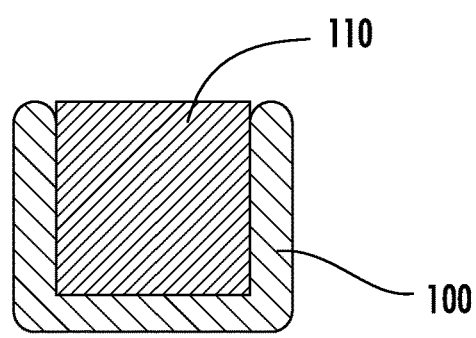
FIG. 6 is a cross-sectional view along line VI-VI in FIG. 4 of a portion of a strut of a heart valve implant with an annulus patch formed in accordance with various principles of the present disclosure provided thereon.

In accordance with principles of the present disclosure, an annulus patch 100, 200 formed in accordance with principles of the present disclosure may be predisposed on the frame member 1100 of the heart valve implant device 1000 to be delivered therewith to the treatment site TS. As illustrated in FIG. 4, an annulus patch 100 which extends around substantially all of the perimeter of the heart valve implant device 1000 may be delivered collapsed and folded on the frame member 1100. The annulus patch 100 may closely follow the struts 1110 (as illustrated in FIG. 4), such as a result of elastomeric properties thereof, or may more loosely follow the struts 1110 (e.g., not adjacent or against the struts 1110 along the entire frame member 1100), such as if the annulus patch 100 is formed from a less elastomeric, or a substantially noncompliant material. The collapsed frame member 1100 of the heart valve implant device 1000 may carry the annulus patch 100 along the distal end 1101 thereof, such as substantially following the sinusoidal or zig-zag shape of the struts 1110 and folded between adjacent struts 1110, as illustrated in the detail view of FIG. 5. The folded annulus patch 100 may pull away from portions of the struts 1110 not engaging the valve annulus VA and move into engagement with the valve annulus VA upon deployment (e.g., including expansion) of the heart valve implant device 1000. The annulus patch 100 may become taut or somewhat taut upon expansion of the heart valve implant device 1000 for implanting with or application to the valve annulus VA. In some embodiments, the annulus patch 100 may wrap around the struts 1110, as illustrated in the detail view of FIG. 6 (in the illustrated example, the strut has a non-circular cross-sectional shape and the annulus patch 100 wraps around more than one side of the strut 1110). The frame member 1100 may retain the annulus patch 100 thereon between the struts 1110. Additionally or alternatively, the anchors 1120 hold the annulus patch 100 onto the frame member 1100. Additional or alternative modes of retaining the annulus patch 100 on the heart valve implant device 1000 (e.g., adhesive, sutures, hook and loop material, reversible adhesion releasing agents, and/or other bonding features acceptable for use within the body and known or heretofore known in the art) are within the scope of the present disclosure as well.

Figure 7:
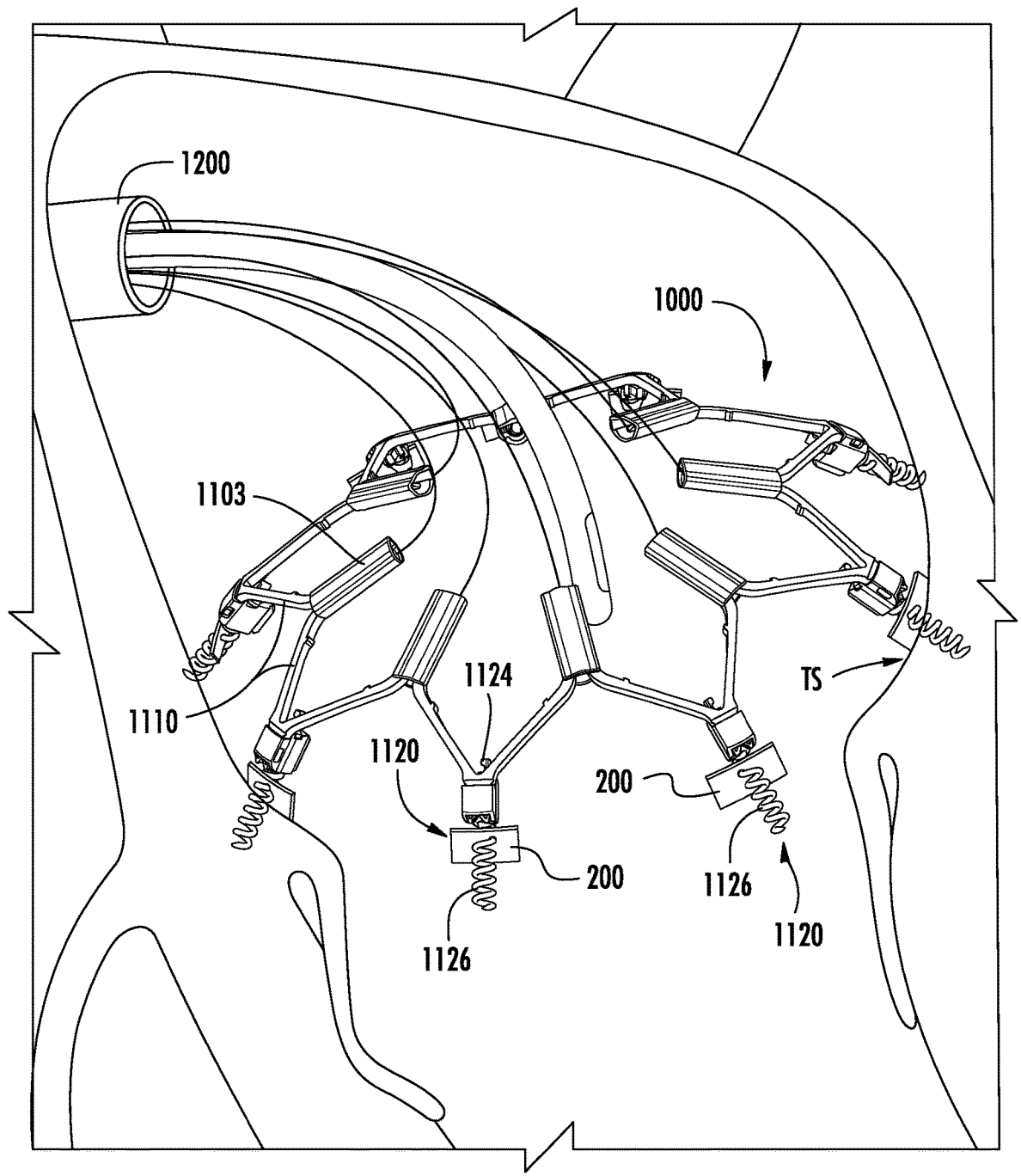
FIG. 7 is a perspective view of a heart valve implant carrying another embodiment of an annulus patch in accordance with various aspects of the present disclosure.

With regard to the embodiment of annulus patch 200 illustrated in FIG. 2, individual patch segments may be carried on an anchor 1120 of a heart valve implant device 1000 during delivery of the heart valve implant device 1000 to a treatment site TS. For example, as illustrated in FIG. 7, the anchor may have an anchor head 1124 (engageable with a driver or actuator, not shown, for driving the anchor into the valve annulus VA) and an anchor shaft 1126 (illustrated in this embodiment as helical, however other configurations are within the scope of the present disclosure). As may be appreciated, the annulus patch 200 may be flexible, and need not maintain a flat configuration before delivery (e.g., may extend or droop downwardly). Upon contacting tissue at the treatment site TS, the annulus patch 200 may be extended (or otherwise configured) into the desired contact with the treatment site TS upon expansion of the frame member 1100.

Figure 8A:
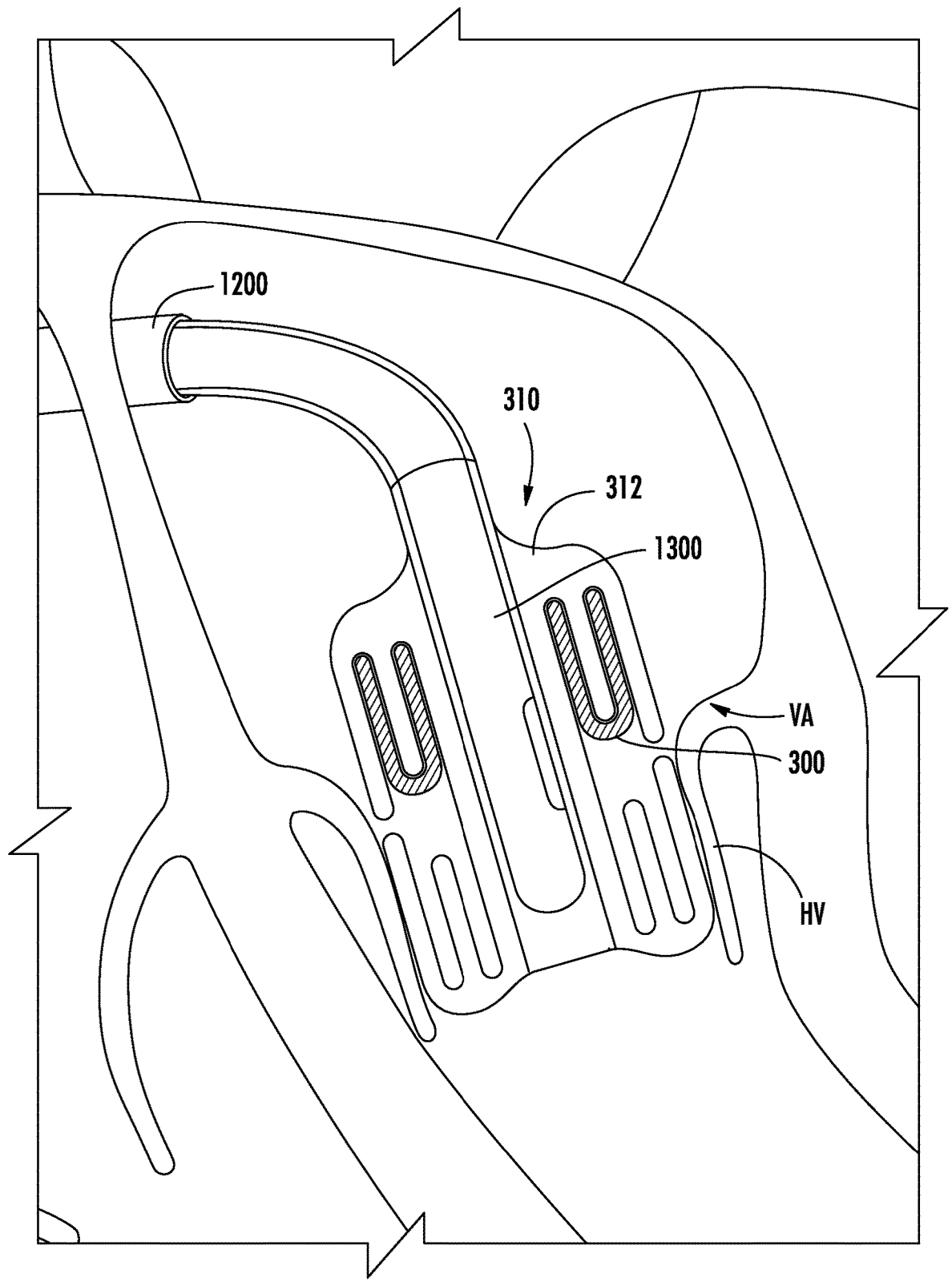
FIGS. 8A-8C are schematic views of a human heart valve with an embodiment of a heart valve implant delivery device shown deploying an annulus patch in accordance with various principles of the present disclosure.
Figure 8B:
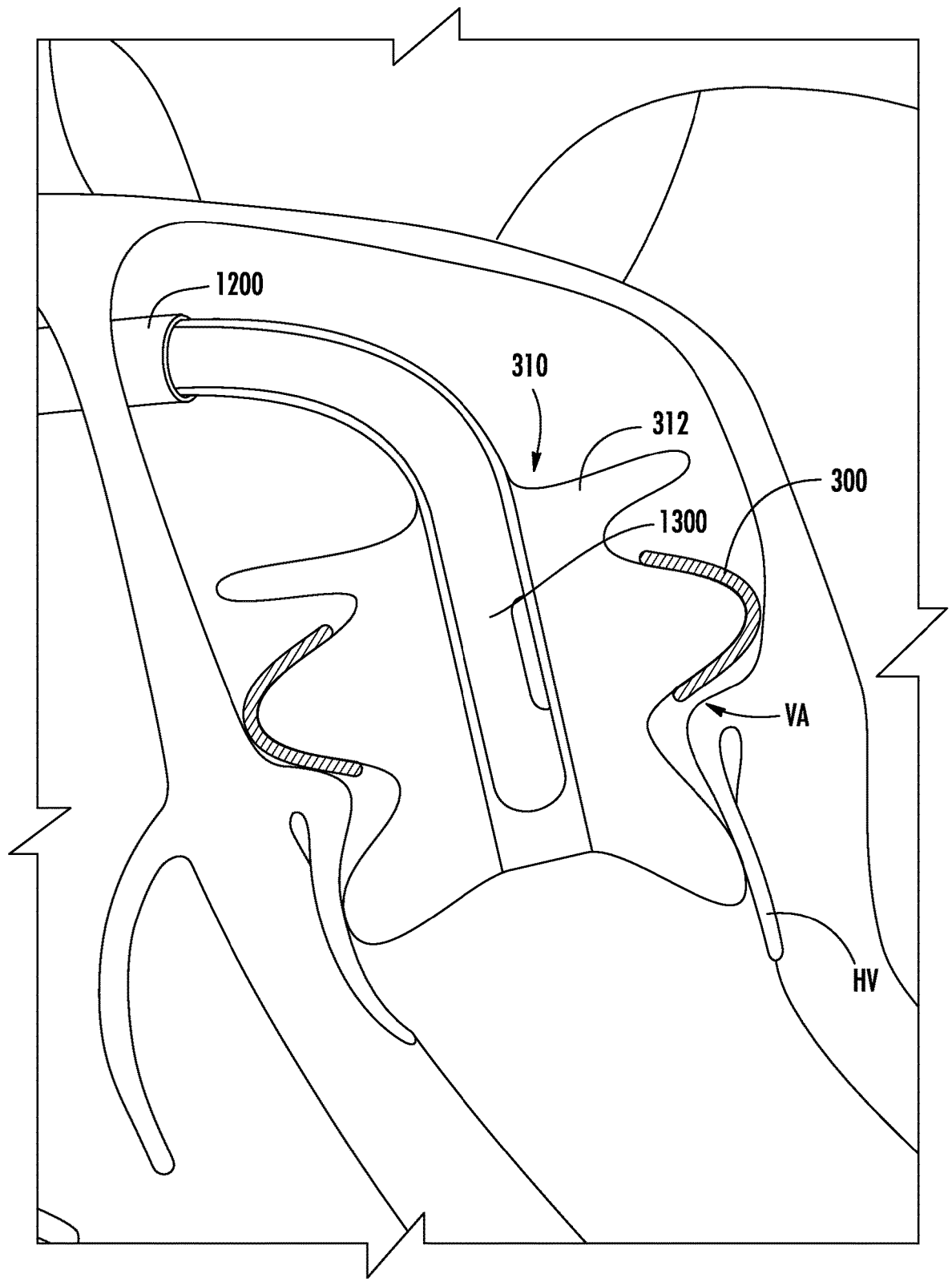
Figure 8C:
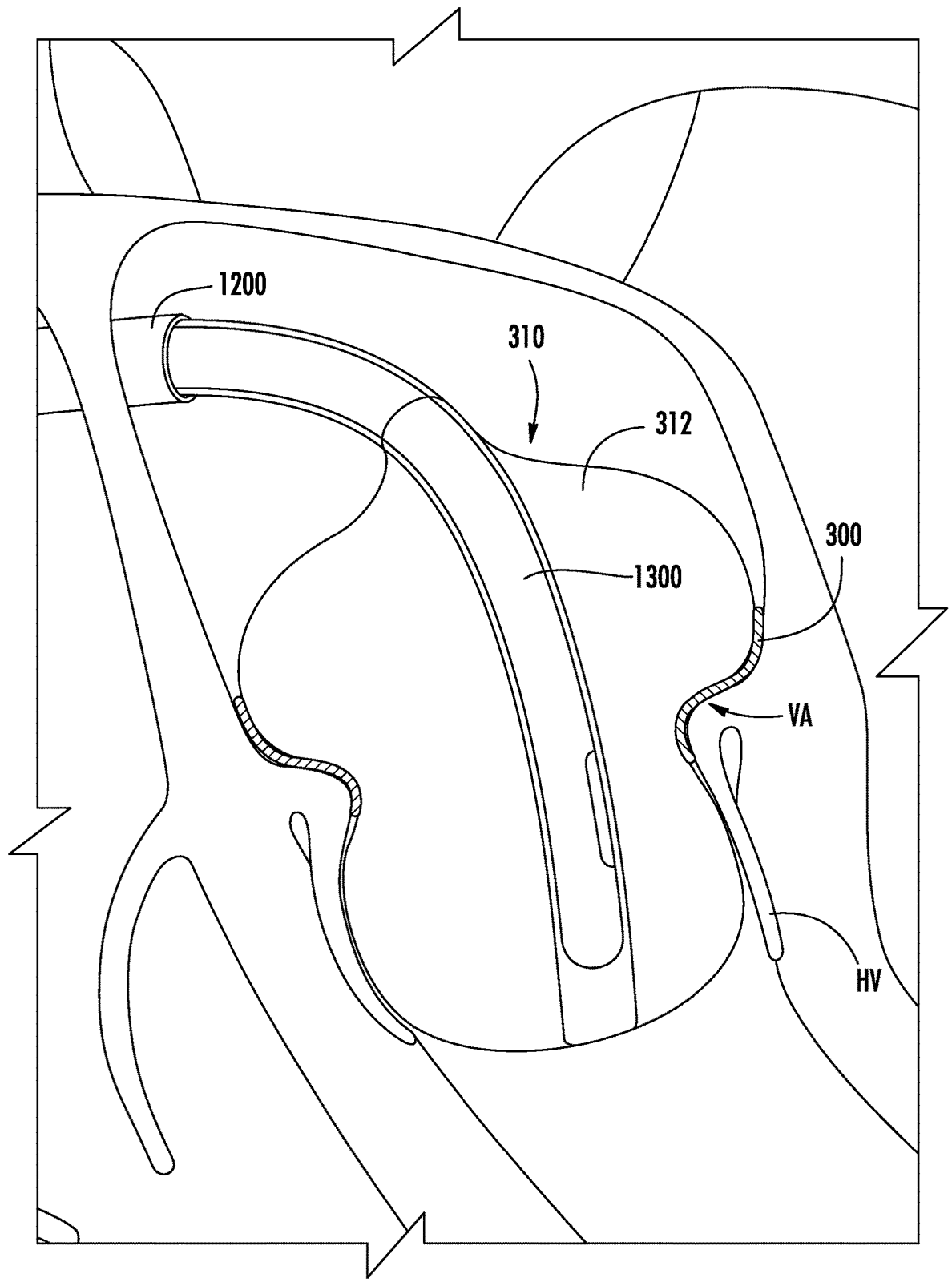
Figure 9:
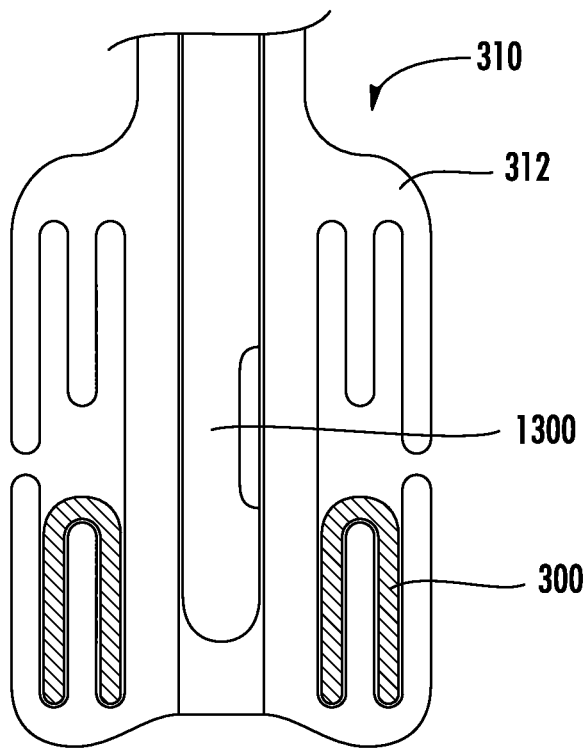
FIG. 9 is a view similar to FIG. 8A but with an alternate configuration of an annulus patch formed in accordance with various principles of the present disclosure.

Instead of being delivered with the heart valve implant device 1000 (such as being carried on or otherwise associated with the heart valve implant device 1000 during delivery thereof to the treatment site TS), an annulus patch formed in accordance with principles of the present disclosure may be pre-disposed on a delivery device and delivered and placed at the treatment site TS before the heart valve implant device 1000 is delivered and placed, as illustrated in FIGS. 8A-8C and FIG. 9. As shown in FIG. 8A and FIG. 8B, an annulus patch 300 is illustrated pre-disposed on a delivery device 310 including a delivery balloon 312. The annulus patch 300 may be similar to the annulus patch 100 of FIGS. 1 and 3 in that the annulus patch 100 extends substantially continuously around the delivery device 310 for delivery around the perimeter of the valve annulus VA (e.g., substantially continuously around the perimeter of the valve annulus VA, as well as substantially continuously about a heart valve implant device to be implanted therein). The delivery balloon 312 is delivered in a compact configuration (e.g., folded or compressed), such as through a delivery catheter 1200. As may be appreciated with respect to FIG. 8A, the annulus patch 300 may be carried by the folds of the delivery balloon 312 and may be folded along with (following, over, in correspondence with, etc.) the folds of the delivery balloon 312. The delivery balloon 312 is extended or expanded or inflated (such terms being used interchangeably herein without intent to limit) to reconfigure the annulus patch 300 for proper placement. As illustrated in FIG. 8B, the delivery balloon 312, in a partially expanded configuration, is positioned with respect to the valve annulus VA, such as with the annulus patch 300 substantially aligned with the valve annulus VA, to place the annulus patch 300 at the desired position on the valve annulus VA. The inflated delivery balloon 312 places the annulus patch 300 on the valve annulus VA, as illustrated in FIG. 8C, to deploy the annulus patch 300 in position to receive the heart valve implant device 1000. Various release mechanisms which may be used to deploy the annulus patch 300 from the delivery balloon 312 (e.g., to detach the annulus patch 300 if adhered or otherwise held in place on the delivery balloon 312) include, without limitation, temperature, fluid, chemical catalyst, and/or, mechanical activation, or other bioactivated release in accordance with manners and methods known in the field. The annulus patch 300 may be provided with or configured to have instant tissue bond/release action elements which may be protected within the delivery balloon 312 folds while the annulus patch 300 is delivered in the folded configuration illustrated in FIG. 8B. The heart valve implant device 1000 may be implanted immediately thereafter, or after an indicated period of time such as a few days or even a few weeks.

It will be appreciated that the above-described manner of delivering an annulus patch 300 prior to delivering a heart valve implant device 1000 to a treatment site TS may use devices and systems other than the illustrated and described balloon delivery device. Moreover, devices providing imaging capabilities as described above (such as an intravascular cardiac echography (ICE) catheter 1300) may be used to monitor placement of the annulus patch 300 during deployment.

Figure 10:
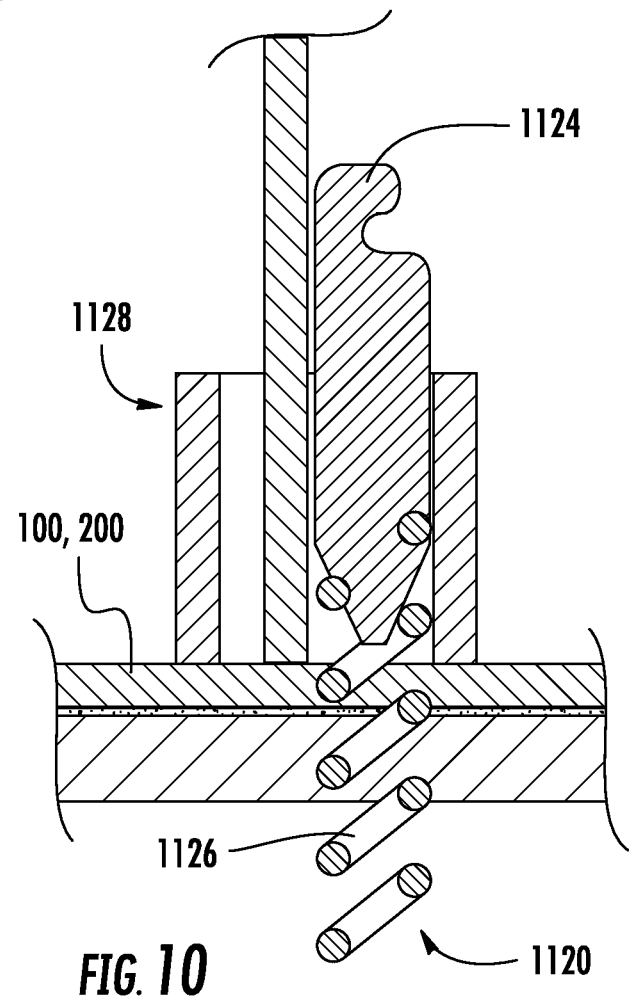
FIG. 10 is an isolated cross-sectional view of an anchor of a heart valve implant device anchored into annulus valve tissue with an annulus patch formed in accordance with various principles of the present disclosure between the heart valve implant device 1000 and the annulus valve tissue.

Once the heart valve implant device 1000 and annulus patch 100, 200, 300 formed in accordance with principles of the present disclosure have been deployed, as illustrated in FIG. 10, the annulus patch 100, 200, 300 is positioned between the heart valve implant device 1000 and the valve annulus VA to provide various benefits such as described above, such as resisting movement of the heart valve implant device 1000 upon deployment at the treatment site TS and/or as the heart valve implant device 1000 is being secured at or implanted in the treatment site TS, and/or reinforcing tissue at the treatment site TS, and/or protecting tissue at the treatment site TS from possible abrasion from implanting of the heart valve implant device 1000 therein (e.g., upon rotation of an anchor 1120 relative to the treatment site TS). Preferably, the annulus patch 100, 200, 300 itself resists movement during implant of the implantable device in the treatment site TS such as by rotation of anchor 1120 relative to the treatment site TS as well as relative to the annulus patch 100, 200, 300. The implantable device 1000 may then be secured, in position over the annulus patch 100, 200, 300, to the treatment site TS. Portions or regions of the implantable device 1000 contacting the treatment site TS may thus contact the treatment site TS via or through the annulus patch 100, 200, 300 (i.e., with the annulus patch 100, 200, 300 interposed therebetween) to inhibit lateral shifting of the implantable device 1000 without interfering with contact with the treatment site TS such as in a direction normal to the treatment site TS.

Although embodiments of the present disclosure may be described with specific reference to mitral valves, a patch such as disclosed herein may be used in connection with repair or modification of any valve annulus, for example including a tricuspid valve annulus, and/or may similarly benefit any other dilatation, valve incompetency, valve leakage, and other similar heart failure conditions which involve anchoring a component to heart tissue. It will be further appreciated that although embodiments of patches are described with respect to heart valve implant devices, the principles of the present disclosure may be applied to patches used in connection with other types of devices used in the body, such as implanted in the body, particularly in areas with soft tissue and/or regular movement of the tissue in which the implant is located.

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another. The following claims are hereby incorporated into this Detailed Description by this reference, with each claim standing on its own as a separate embodiment of the present disclosure. Reference signs in the claims are provided merely as a clarifying example and shall not be construed as limiting the scope of the claims in any way.

The following claims are hereby incorporated into this Detailed Description by this reference, with each claim standing on its own as a separate embodiment of the present disclosure. In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "the", "first", "second", etc., do not preclude a plurality. Reference signs in the claims are provided merely as a clarifying example and shall not be construed as limiting the scope of the claims in any way.

What is claimed is:

1. A heart valve implant device comprising: a frame having a proximal end and a distal end and configured to be implanted in a valve annulus surrounding a heart valve; a plurality of anchors carried by the frame and configured to anchor the frame with respect to a valve annulus; and a plurality of patches carried by the frame to engage the plurality of anchors, wherein an anchor of the plurality of anchors extends through each patch of the plurality of patches to engage the valve annulus to position the plurality of patches between the frame and the valve annulus.

2. The device of claim 1, wherein:
the frame comprises a plurality of distal apices formed at the distal end thereof;

the frame is secured to the valve annulus along the distal apices; and the plurality of patches are is positioned along distal apices to be positioned between the distal apices and the valve annulus when the frame is secured to the valve annulus.

3. The device of claim 2, wherein the plurality of patches discontinuously extend about a perimeter of the frame.

4. The device of claim 3, wherein:

each of the plurality of anchors is positioned at a distal apex of the frame; and at least one of the patches is carried by an anchor at a distal apex of the frame.

5. The device of claim 2, wherein each of the anchors has a proximal end coupled to a distal apex of the frame and extends distally through a patch to engage the valve annulus with the patch between the distal apex and the valve annulus.

6. The device of claim 1, wherein the frame is configured to move between a collapsed delivery configuration and an expanded configuration and positions therebetween to modify the shape of a valve annulus to which the frame is secured.

7. The device of claim 6, wherein:

the frame comprises a plurality of struts joined along proximal apices at the proximal end of the frame and distal apices along the distal end of the frame;

each of the plurality of anchors is positioned at a distal apex of the frame; and at least one of the anchors carries one of the plurality of the patches.

8. The device of claim 7, wherein the plurality of patches comprises a plurality of patches discontinuously extending about a perimeter of the frame, at least one of the patches being carried by an anchor.

9. The device of claim 1, wherein each of the plurality of anchors extends through a patch of the plurality of patches.

10. The device of claim 1, wherein the plurality of patches is configured to collapse and fold with the frame when the frame is in a collapsed delivery configuration.

11. A heart valve implant device comprising: a frame; a plurality of anchors each having a proximal end carried by the frame and a distal end extending distally away from the frame; a plurality of patches positioned between the implantable device and the treatment site with at least one of the plurality of anchors extending from the proximal end of the anchor coupled to the frame through a patch of the plurality of patches to a distal end of the anchor.

12. The device of claim 11, wherein the patch is carried by the implantable device.

13. The device of claim 11, wherein the implantable device comprises a plurality of distal apices formed at the distal end thereof, the at least one of the plurality of anchors extending distally from a distal apex of the distal apices, through the patch, and into the treatment site.

14. The device of claim 11, wherein the patch is configured to extend around a perimeter of the treatment site.

15. The device of claim 14, wherein the patch is a substantially continuous ring configured to extend continuously around the perimeter of the treatment site.

16. The device of claim 14, wherein the patch is configured to extend discontinuously around the perimeter of the treatment site.

17. The device of claim 11, wherein the implantable device is an annuloplasty device configured to move between a collapsed delivery configuration and an expanded configuration and positions therebetween to modify the shape of a valve annulus.

18. An annuloplasty method comprising: deploying a heart valve implant device around a valve annulus and implanting the heart valve implant device into the valve annulus with a plurality of annulus patches and implanting the heart valve implant device into the valve annulus with the annulus patch positioned between the valve annulus and portions of heart valve implant device; engaging the valve annulus via the annulus patches and a plurality of anchors coupled to the heart valve implant device and extending an anchor through a patch of the plurality of patches and into the valve annulus and adjusting the configuration of the heart valve implant device to modify the shape of the heart valve annulus to repair the function of the native heart valve.

19. The method of claim 18, further comprising delivering the annulus patch with the heart valve implant device to the valve annulus.

20. The method of claim 18, further comprising delivering and deploying the annulus patch before delivering and deploying the heart valve implant device.

* * * * *